United States Patent [19]

Richards et al.

[11] 4,448,762

[45] May 15, 1984

[54] COMPLEX OF TRANSFERRIN WITH RUTHENIUM FOR MEDICAL APPLICATIONS

[75] Inventors: Powell Richards, Bayport; Suresh C. Srivastava, Setauket; George E. Meinken, Middle Island, all of N.Y.

[73] Assignee: The United States of America as represented by the United States Department of Energy, Washington, D.C.

[21] Appl. No.: 203,194

[22] Filed: Nov. 3, 1980

[51] Int. Cl.$^3$ .................... A61K 49/00; A61K 43/00
[52] U.S. Cl. ......................... 424/1.1; 424/9; 260/112 B
[58] Field of Search .................. 424/1, 9; 260/112 B

[56] References Cited

U.S. PATENT DOCUMENTS

| 3,939,258 | 2/1976 | Niemann | 424/1 |
| 4,057,617 | 8/1977 | Abramovici et al. | 424/1 |
| 4,162,142 | 7/1979 | Ehrenkaufer et al. | 424/1 |

OTHER PUBLICATIONS

Subramanian et al., J. Nucl. Med., vol. 11, p. 365, (1970).
Radio Pharmaceuticals II: Proc. 2nd Int. Symposium on Radio Pharmaceuticals, (Mar. 1979), pp. 265-274.
Anghileri, Strahlentherapic, vol. 149, pp. 173-175, (1975).
Tanabe, Radio Isotopes, vol. 25, pp. 44-49, (1976).
Tanabe, Acta Medica Okayama, vol. 29, pp. 431-436, (1975).
Srivastava et al., Paper #BNL 27794, DOE, Mar. 1980.
Srivastava et al., Paper #BNL 27285, DOE, Jun. 1980.
Som et al., Paper #BNL 27969, DOE, Oct. 1980.
Oster et al., Paper #BNL 27737, DOE, Sep. 1980.

*Primary Examiner*—Christine M. Nucker
*Attorney, Agent, or Firm*—Margaret C. Bogosian; James W. Weinberger; Michael F. Esposito

[57] ABSTRACT

A novel Ruthenium-transferrin complex, prepared by reacting iron-free human transferrin dissolved in a sodium acetate solution at pH 7 with ruthenium by heating at about 40° C. for about 2 hours, and purifying said complex by means of gel chromotography with pH 7 sodium acetate as eluent. The mono- or di-metal complex produced can be used in nuclear medicine in the diagnosis and/or treatment of tumors and abscesses. Comparative results with Ga-67-citrate, which is the most widely used tumor-localizing agent in nuclear medicine, indicate increased sensitivity of detection and greater tumor uptake with the Ru-transferrin complex.

9 Claims, No Drawings

COMPLEX OF TRANSFERRIN WITH RUTHENIUM FOR MEDICAL APPLICATIONS

The United States Government has rights in this invention pursuant to Contract Number DE-AC02-76CH00016 between the U.S. Department of Energy and the Brookhaven National Laboratory, Associated Universities, Inc.

BACKGROUND OF THE INVENTION

The present invention relates to novel ruthenium labeled transferrin compounds, methods for preparing and purifying them, and their uses in nuclear medicine as a diagnostic tool, as well as possible uses in the treatment of tumors and abscesses.

The prior art discloses the labeling of proteins with Technetium-99 (Tc-99) to produce an injectable isotopic tracer as described in U.S. Pat. No. 4,057,617; and the labeling with tritium is described in U.S. Pat. No. 4,162,142. The labeling of transferrin with Indium-113 (In-113) for purposes of measuring circulation and visualizing the placenta is described in U.S. Pat. No. 3,939,258. However, there is no disclosure of a ruthenium transferrin complex.

Even though short-lived radionuclides, in particular Tc-99m, have found extensive application in nuclear medicine, intermediate half-life nuclides may be extremely valuable for diagnostic studies at longer time intervals. Many nuclear medicine procedures indeed require delayed scanning or frequent imaging over a long time period in order to obtain diagnostically important information. Ruthenium-97 is an ideal nuclide for such applications; its potential in nuclear medicine was first suggested by Subramanian et al in 1970 (G. Subramanian, J. G. McAfee, and J. K. Poggenburg, Ru-97: Preliminary evaluation of a new radionuclide for use in nuclear medicine. J. Nucl. Med. 11:365 (1970) (Abstract)). The 2.9 day half-life and an essentially monoenergetic gamma emission (216 DeV, 86%), in conjunction with the chemical reactiveness of ruthenium provide an extremely useful combination. The 2.9 day half-life of Ruthenium-97 makes many studies and procedures possible, not otherwise practical with Technetium-99m. In many ways, the physical characteristics of Ru-97 are superior to those of Gallium-67 (Ga-67) and In-111.

Gallium-67 citrate is presently the most widely used agent for tumor localization. This agent has serious disadvantages, however. It does not concentrate selectively in tumors, the background remains high, and its imaging properties are far from ideal. As clinical trails have progressed, it has become evident that gallium-67 citrate concentrates in a variety of normal structures and in several diverse benign and malignant pathologic lesions. This lack of specificity has made the interpretation of gallium-67 scans difficult.

SUMMARY OF THE INVENTION

The object of the invention is to solve the existing disadvantages by utilizing a novel ruthenium labeled transferrin compound for the localization and imaging of tumors, abscesses, inflammatory tissue, and other conditions in the body where there is a mechanism involving transferrin-mediated transport of the ruthenium.

Another object is to produce a new complex (mono or di-ruthenium) of transferrin with ruthenium radionuclides.

Another object is to produce a radioactive ruthenium transferrin complex suitable for medical applications, both diagnostic and therapeutic.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purpose of the present invention, as embodied and broadly described herein, the novel complex of transferrin with ruthenium of this invention comprises the mono- and/or di-ruthenium labeled monomeric transferrin. Transferrin is a blood protein of high molecular weight and can complex with one or two metal ions, since it contains two predominant binding sites. Preferably, transferrin is labeled with ruthenium radionuclides, such as beta-emitting ruthenium-103 or -106 having therapeutic applications, or gamma-emitting ruthenium-97 having diagnostic applications in the localization and imaging of tumors, abscesses and the like.

The ruthenium-transferrin complex is prepared by reacting iron-free human transferrin dissolved in a pH 7 sodium acetate solution with carrier-free ruthenium activity, preferably complexed with NTA (Nitrilotriacetic acid or similar sequestering agent), at a temperature of about 40°-65° C. and preferably 40° C. for about 1-2 and preferably 2 hours, and the resultant complex is purified by means of gel chromatography (a column of porous material which removes degradation products and other impurities) with pH 7 sodium acetate in saline as eluent to obtain pure monomeric Ruthenium (Ru) labeled transferrin. The complexing agent protects the ruthenium from hydrolysis, thereby ensuring a better yield of the ruthenium-transferrin complex.

Most initial investigations were carried out using ruthenium-103 due to its convenient 39.6 day half life. Carrier-free ruthenium-103 chloride was obtained from the Oak Ridge National Laboratory as a solution in 3.5 N hydrochloric acid. Ruthenium-97 was prepared as needed at the BLIP (Brookhaven Linac Isotope Producer) from proton spallation of high purity (greater than 99.9%) rhodium foil. The target was bombarded with 200 MeV protons from the Linac. After the bombardment, the target was transferred to a processing hot cell and dissolved by a.c. electrolysis in 6 N hydrochloric acid (0.3 A/cm$^2$, about 15 hrs). After evaporating the solution to near dryness, radio-chemical separation of ruthenium-97 was achieved by distillation of $RuO_4$ from a sulfuric acid medium in the presence of permanganate. The distillate was collected in ice cold ethanol-hydrochloric acid (1:1). Recovery of the ruthenium-97 from the target was almost quantitative.

Initial studies on a number of ruthenium compounds as diagnostic tumor localizing agents have demonstrated high concentration into the mouse subcutaneous EMT-6 sarcoma and in several other animal tumor models. The uptake on a per gram basis of carrier-free ruthenium-103 chloride and a variety of other ruthenium compounds in the EMT-6 sarcoma was comparable to that of gallium-67 citrate and the uptake of ruthenium labeled transferrin was almost twice as high as that of gallium at comparable time periods. It is likely that the simple ruthenium compounds are transported to various tissues (including tumor) after being predominantly bound to transferrin. If, according to prevailing hypothesis, the EMT-6 sarcoma concentrates gallium via a transferrin-mediated mechanism, it could follow that ruthenium, because of its strong binding to transferrin, will localize preferentially in tumor tissue and, in addition, that transferrin labeled in vitro with ruthenium would produce a higher degree of tumor uptake.

When ruthenium chloride is administered intravenously, a major portion of it becomes bound to transferrin and is initially transported to various tissues intact as the ruthenium-transferrin complex. Apparently, the in-vivo kinetics of this binding is not very favorable; the result is non-specific localization of a significant part of the ruthenium activity in other tissues. When in-vitro labeled ruthenium transferrin is injected, a more specific tumor uptake results with diminished background activity.

Recent in-vitro studies on the ruthenium-labeled transferrin point to the predominance of monoruthenium transferrin in our preparations. It is known that transferrin which has both available metal binding sites occupied, binds to the cell surface receptors more avidly than monometallic transferrin. The active transport of ruthenium could then be enhanced by metallating both the transferrin metal binding sites with ruthenium; in addition, the total uptake of the activity by the tumor thus could be doubled.

The data obtained so far support the conclusion that ruthenium-97 labeled transferrin is a potential new agent for scintigraphic delineation of tumors. Uptake of this material in several mouse tumor models is almost twice as high as that of gallium citrate. Additionally, the imaging characteristics of ruthenium-97 are far superior to those of gallium-67. The sensitivity of detection of the tumor with the ruthenium labeled transferrin in the tumor models studied is increased five times over that of the gallium citrate.

DETAILED DESCRIPTION OF THE INVENTION

The following examples are merely illustrative of the invention, and are not to be construed as limiting thereof.

EXAMPLE 1

A Ruthenium-103 labeled transferrin:

Twenty mg purified iron-free human transferrin (Sigma) is dissolved in 2 ml of a 0.1 M, pH 7 sodium acetate solution. The desired amount of carrier-free ruthenium activity (Ru-103 in about 3 N HCl) is added to a vial and the HCl blown off with nitrogen under gentle heating. A two fold molar excess, over that of ruthenium, of a suitable complexing agent (Nitrilotriacetic acid, NTA, preferably was used) is added, the pH adjusted to 2.5-3, and the solution heated at 90°-100° C. for 30 minutes. The pH is adjusted to 6-7. The dissolved transferrin in acetate buffer is then added to the cooled ruthenium vial followed by 0.1 ml of 0.1 M sodium bicarbonate. The mixture, final volume about 3 ml, pH about 7.5-8, is heated at 40° C. for 2 hrs. The preparation is purified on a 0.9×100 cm G-150 Sephadex column (contains a porous gel of polysaccharides) with 0.154 M NaCl-0.005 M pH 7 sodium acetate as the eluent resulting in a 60-90% yield of monomeric labeled transferrin. The purity of this fraction is at least 90% by polyacrylamide gel electrophoresis (a method of separation, purification and identification by means of migration of particles in an electric field).

Ru-103 has a 39.4 day half-life and was obtained from the Oak Ridge National Laboratory as a carrier-free solution of Ru-103 chloride in 3.5 N hydrochloric acid.

EXAMPLE 2

A Ruthenium-97 labeled Transferrin:

The procedure described in Example 1 is used except that Ruthenium-97 produced in BLIP was substituted for Ruthenium -103.

Any natural ruthenium isotope may be substituted for the Ruthenium-97 in the above example in the production of a ruthenium labeled transferrin.

The ruthenium labeled transferrin compounds are administered by injection into the test animals. Tissue distribution data were obtained in normal and tumor-bearing animals (mice, rats, hamsters). The tumor model most extensively utilized was the subcutaneous EMT-6 sarcoma in Balb/c mice. The tumor uptake is quite high at 24-72 hrs after injection.

TABLE 1

Tissue Uptake of Ruthenium-103 Labeled Transferrin[a,b] in EMT-6 Sarcoma Mice

Percent dose per g (n = 6)

| Tissue | Time after injection, hr | | | | |
|---|---|---|---|---|---|
| | 1 | 6 | 24[c] | 48 | 72 |
| Blood | 43.27 ± 5.11 | 23.73 ± 2.20 | 12.89 ± 0.58 | 4.56 ± 0.34 | 2.49 ± 0.37 |
| Tumor | 4.90 ± 0.39 | 8.67 ± 0.52 | 12.75 ± 0.70 | 13.34 ± 0.60 | 12.39 ± 1.59 |
| Liver | 10.36 ± 0.76 | 12.26 ± 1.20 | 8.85 ± 0.77 | 7.46 ± 0.57 | 6.06 ± 0.44 |
| Kidney | 11.55 ± 1.47 | 8.92 ± 0.48 | 8.42 ± 0.45 | 7.16 ± 0.49 | 6.14 ± 0.41 |
| Muscle | 0.83 ± 0.12 | 1.38 ± 0.19 | 1.57 ± 0.21 | 1.32 ± 0.14 | 1.07 ± 0.13 |
| Heart | 6.97 ± 0.67 | 4.60 ± 0.32 | 3.81 ± 0.25 | 2.47 ± 0.20 | 1.92 ± 0.10 |
| Spleen | 9.81 ± 0.73 | 9.12 ± 0.56 | 8.74 ± 0.52 | 7.30 ± 0.77 | 5.77 ± 0.71 |
| Bone | 5.81 ± 0.74 | 4.26 ± 0.38 | 3.56 ± 0.22 | 2.61 ± 0.24 | 2.50 ± 0.27 |
| % Dose remaining in whole body | 81.63 ± 2.26 | 80.02 ± 1.95 | 66.61 ± 2.99 | 55.88 ± 2.62 | 44.21 ± 2.80 |

[a]Purified on Sephadex G-150 (0.9 × 100 cm) column. Fraction used here contained essentially monomeric transferrin with about 65% of the original ruthenium activity associated with it.
[b]Dose of transferrin ~3.3 mg/Kg body wt.
[c]n = 11
n. number of test animals

TABLE 2

Tissue Uptake of Gallium-67 Citrate in EMT-6 Sarcoma Mice

Percent dose per g (n = 6)

| Tissue | Time after injection, hr | | | | |
|---|---|---|---|---|---|
| | 6 | 24 | 48 | 72 | 96 |
| Blood | 11.17 ± 1.03 | 1.81 ± 0.22 | 0.51 ± 0.07 | 0.44 ± 0.03 | 0.36 ± 0.07 |
| Tumor | 6.01 | 7.09 | 5.05 | 4.53 | 3.54 |

TABLE 2-continued

Tissue Uptake of Gallium-67 Citrate in EMT-6 Sarcoma Mice
Percent dose per g (n = 6)

| Tissue | Time after injection, hr | | | | |
|---|---|---|---|---|---|
| | 6 | 24 | 48 | 72 | 96 |
| Liver | ± 0.74 | ± 0.69 | ± 0.46 | ± 0.34 | ± 0.62 |
| | 8.52 | 9.30 | 9.49 | 8.35 | 8.19 |
| Kidney | ± 0.64 | ± 0.95 | ± 1.57 | ± 1.09 | ± 1.10 |
| | 7.44 | 9.21 | 8.03 | 7.50 | 7.14 |
| Muscle | ± 0.66 | ± 0.82 | ± 0.63 | ± 0.73 | ± 1.25 |
| | 0.87 | 0.53 | 0.47 | 0.47 | 0.37 |
| Heart | ± 0.08 | ± 0.002 | ± 0.004 | ± 0.08 | ± 0.06 |
| | 3.09 | 2.21 | 1.69 | 1.82 | 1.51 |
| Spleen | ± 0.29 | ± 0.27 | ± 0.10 | ± 0.14 | ± 0.52 |
| | 5.78 | 8.37 | 6.60 | 6.52 | 5.41 |
| Bone | ± 0.81 | ± 0.91 | ± 0.78 | ± 1.13 | ± 1.06 |
| | 16.16 | 17.75 | 17.55 | 15.38 | 12.66 |
| % Dose remaining in whole body | ± 1.05 | ± 2.50 | ± 1.40 | ± 2.30 | ± 1.12 |
| | 65.23 | 59.58 | 50.68 | 43.91 | 38.29 |
| | ± 0.79 | ± 1.72 | ± 0.21 | ± 1.69 | ± 2.69 |

TABLE 3

Tumor-to-Blood and Tumor-to-Tissue Ratios of Ruthenium-103-Transferrin and Gallium-67-Citrate in EMT-6 Sarcoma Mice (n = 6)

| Compound | Time post injection, hr | Ratio, tumor to | | | |
|---|---|---|---|---|---|
| | | Blood | Muscle | Liver | Kidney |
| Ruthenium-103 transferrin | 1 | 0.12 ± 0.01 | 6.37 ± 0.89 | 0.48 ± 0.03 | 0.44 ± 0.04 |
| | 6 | 0.37 ± 0.02 | 6.61 ± 0.64 | 0.72 ± 0.04 | 0.97 ± 0.05 |
| | 24 | 1.00 ± 0.07 | 8.76 ± 1.10 | 1.48 ± 0.12 | 1.52 ± 0.07 |
| | 48 | 2.97 ± 0.14 | 10.63 ± 1.27 | 1.83 ± 0.15 | 1.89 ± 0.12 |
| | 72 | 5.04 ± 0.15 | 11.79 ± 1.16 | 2.04 ± 0.20 | 2.01 ± 0.18 |
| Gallium-67 citrate | 6 | 0.53 ± 0.003 | 7.30 ± 1.05 | 0.71 ± 0.06 | 0.82 ± 0.08 |
| | 24 | 4.17 ± 0.58 | 13.36 ± 1.52 | 0.81 ± 0.12 | 0.77 ± 0.06 |
| | 48 | 10.70 ± 1.86 | 11.04 ± 1.25 | 0.56 ± 0.06 | 0.63 ± 0.05 |
| | 72 | 10.66 ± 1.24 | 10.78 ± 2.07 | 0.57 ± 0.06 | 0.61 ± 0.04 |
| | 96 | 10.33 ± 1.36 | 10.55 ± 2.25 | 0.40 ± 0.07 | 0.51 ± 0.04 |

TABLE 4

Tumor Concentration Index* of Ruthenium-103-Labeled Transferrin In EMT-6 Sarcoma, Balb/c mice. Ruthenium-103 Chloride and Gallium-67-Citrate are included for Comparison.

| Compound | TCI | | | |
|---|---|---|---|---|
| | 24 hr | 48 hr | 72 hr | 96 hr |
| Ru-103-transferrin | 3.05 | 3.82 | 4.48 | — |
| Gallium-67-citrate | 1.81 | 1.48 | 1.57 | 1.45 |
| Ruthenium-103 chloride | 1.56 | 1.69 | 1.73 | 1.61 |

*Tumor concentration index (TCI) is defined as the ratio of percent injected dose per g in the tumor to percent injected dose per g remaining in the whole body at any given time period. For inter-species comparisons, and for normalizing for different animal body weights, TCI could be expressed as per kg body weight.

Results on the uptake of ruthenium-103-transferrin are described in Table 1. Even though the non target activity (blood, liver, spleen, kidneys) remains substantial, the tumor uptake of this agent is quite high at 24–72 hours after injection resulting in good tumor-to-tissue ratios (Table 3) which was high enough for imaging at 24–72 hours. The distribution of gallium-67 citrate is shown in Table 2 for comparison. Table 4 describes the tumor concentration index (TCI) of various compounds. This index which provides a useful correlation between the tumor uptake and the mean body concentration is defined as the ratio of percent injected dose per g of the tumor to percent injected dose per g remaining in the whole body at any given time period.

The role of radiopharmaceuticals in clinical oncology has been expanding rapidly. As "tumor-scanning" agents, they are useful in the initial staging of tumors and in providing a means of evaluating response to therapy and detecting metastasis or recurrence at early stages before it becomes clinically overt. With the development of improved radiopharmaceuticals, tumor scanning can provide the clinician with a highly sensitive, easy, and safe noninvasive supplement to, or substitute for, other diagnostic procedures. Radionuclides, by themselves or incorporated into tumor seeking compounds, also have additional potential as therapeutic agents.

The use of ruthenium-97 as a scintigraphic agent, in particular for tumor localization, offers several advantages over other isotopes in present use. The half-life of 2.9 days is sufficiently long to allow limited chemical synthesis and purification and not too long to cause excessive radiation dose to the patient. Ruthenium-97 is a pure gamma emitter with an essentially monoenergetic emission of 216 keV (86%). This allows for its use in presently available imaging equipment. Ruthenium-97 has been produced at the Brookhaven Linac Isotope Producer (BLIP) by the Rh-103 (p, 2p5n) Ru-97 reaction. Sufficiently large quantities (over 100 mCi/day) can be produced routinely and economically. The chemistry of ruthenium in its various oxidation states is uniquely suited for the incorporation of this element into a variety of diagnostically useful ligands including biological molecules. Also, reports have appeared on the potential of ruthenium compounds as tumor-localizing agents as shown in the following articles:

1. Srivastava, S C, Richards, P, Meinken, G, et al: Evaluation of radiolabeled ruthenium compounds as tumor-localizing agents, in Radiopharmaceuticals II: Proceedings of the Second International Symposium on Radiopharmaceuticals, New York, Society of Nuclear Medicine, 1979.
2. Anghileri, L J: Radioactive ruthenium red accumulation by tumors: a potential scanning agent. Strahlentherapie 149: 173, 1975.
3. Tanabe, M: Clinical trials on tumor scanning with Ru-103 Radioisotopes 25: 44–49, 1976.
4. Tanabe, M, Yamamoto, G: Tissue distribution of Ru-97 and Ru-103 in subcutaneous tumor of rodents. Acta Medica Okayama 29: 431–436, 1975.

All these facts taken together provide an excellent combination for the application of ruthenium-97 in nuclear medicine, particularly for the development of successful tumor-imaging agents.

Availability of successful ruthenium-97 labeled transferrin will no doubt result in improved diagnostic performance with high information content in the collected images and reduced patient radiation dose when compared to radiopharmaceuticals presently in use.

The foregoing description of a preferred embodiment of the invention has been presented for purposes of illustration and description. It is not intended to be exhaustive or to limit the invention to the precise form disclosed, and obviously many modifications and variations are possible in light of the above teaching. The specific examples were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A mono- or di-metal complex of monomeric transferrin with ruthenium.

2. A metal complex in accordance with claim 1, wherein the ruthenium is radioactive.

3. A metal complex in accordance with claim 2, wherein the ruthenium is a beta-emitting radionuclide selected from the class consisting of Ru-103 and Ru-106.

4. A metal complex in accordance with claim 2, wherein the ruthenium is the gamma emitting radionuclide Ru-97.

5. A method for the preparation of the metal complex of monomeric transferrin of claim 1, wherein iron-free transferrin dissolved in a pH 7 sodium acetate solution is reacted with a carrier-free ruthenium activity, and the resultant Ru complex of monomeric transferrin is purified by means of gel chromotography with pH 7 sodium acetate/saline as the eluent.

6. The method in accordance with claim 5, wherein the transferrin and ruthenium are reacted by heating at about 40° C. for about 2 hours.

7. A method for diagnostic tumor scanning which comprises the intravenous administration of a tumor localizing agent, said tumor localizing agent being a mono- or di- metal complex of monomeric transferrin with radioactive ruthenium, with subsequent imaging of the tumor.

8. The diagnostic method of claim 7 wherein the tumor localizing agent is the Ruthenium-97 metal complex of monomeric transferrin.

9. The diagnostic method of claim 7 wherein the tumor localizing agent is the Ruthenium-103 metal complex of monomeric transferrin.

* * * * *